US006637437B1

(12) United States Patent
Hungerford et al.

(10) Patent No.: US 6,637,437 B1
(45) Date of Patent: Oct. 28, 2003

(54) CELL-CULTURE AND POLYMER CONSTRUCTS

(75) Inventors: David S. Hungerford, Cockeysville, MD (US); Carmelita G. Frondoza, Woodstock, MD (US); Alan H. Shikani, Ruxton, MD (US); Abraham J. Domb, Efrat (IL)

(73) Assignees: Johns Hopkins University, Baltimore, MD (US); Chondros, Inc., Baltimore, MD (US)

( * ) Notice: Subject to any disclaimer, the term of this patent is extended or adjusted under 35 U.S.C. 154(b) by 0 days.

(21) Appl. No.: 09/712,662

(22) Filed: Nov. 14, 2000

Related U.S. Application Data

(63) Continuation-in-part of application No. 09/275,319, filed on Mar. 24, 1999, now Pat. No. 6,378,527.
(60) Provisional application No. 60/165,608, filed on Nov. 15, 1999, provisional application No. 60/104,842, filed on Oct. 20, 1998, and provisional application No. 60/081,016, filed on Apr. 8, 1998.

(51) Int. Cl.[7] .............................................. A61B 19/00
(52) U.S. Cl. ..................................... 128/898; 623/23.72
(58) Field of Search .................. 128/898; 623/23.76, 623/23.72, 14.12

(56) References Cited

U.S. PATENT DOCUMENTS

| 5,041,138 | A | * | 8/1991 | Vacanti et al. ................. 623/16 |
| 5,512,475 | A | | 4/1996 | Naughton et al. ..... 435/240.243 |
| 5,709,854 | A | | 1/1998 | Griffith-Cima et al. .... 424/93.7 |
| 5,786,217 | A | | 7/1998 | Tubo et al. .................. 435/402 |
| 5,919,702 | A | * | 7/1999 | Purchio et al. ............ 424/93.1 |
| 6,082,364 | A | | 7/2000 | Balian et al. ............... 128/898 |
| 6,143,293 | A | | 11/2000 | Weiss et al. ............... 424/93.7 |

* cited by examiner

Primary Examiner—Corrine McDermott
Assistant Examiner—Thomas Barrett
(74) Attorney, Agent, or Firm—Armstrong, Westerman & Hattori, LLP

(57) ABSTRACT

The invention is directed to the culture of cells, and particularly chondrocytes for purpose of tissue replacement. The cells are cultured on polymer constructs. Integren expression is used as a measure of chondrocyte viability. Chondrocytes are obtained from the knee, nose and ankle cartilage. Mechanical strain is used to propagate chondrocytes, chitosan and arabinogalactanchitosan are used as scaffolds. Progenitor, pluripotential, stem and mesenchymal cells are operative in this invention.

4 Claims, 2 Drawing Sheets

CASE # 1

Relative Fluorescence

CASE # 2

Relative Fluorescence

CELL-CULTURE AND POLYMER CONSTRUCTS

RELATED APPLICATIONS

Figure 1:
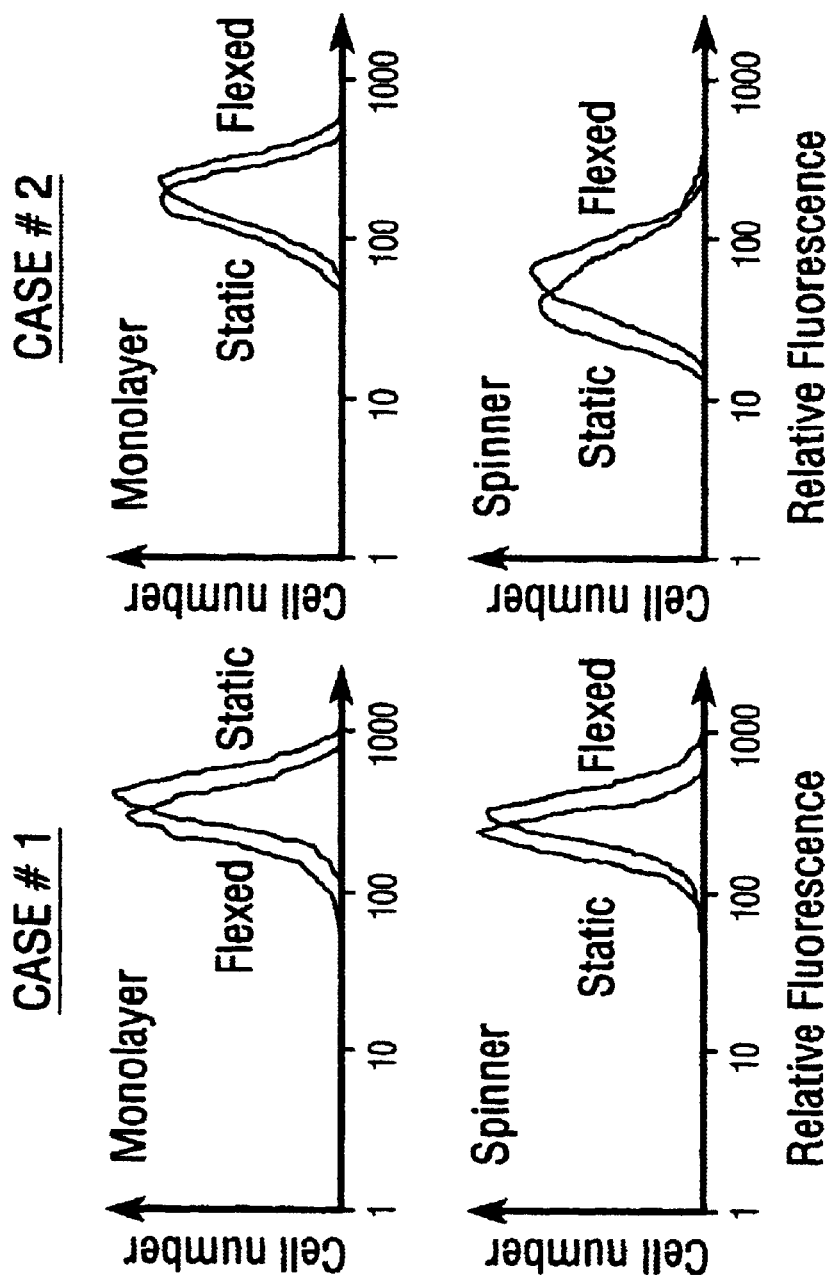

This application is related to provisional applications Serial No. 60/081,016 filed Apr. 8, 1998, Ser. No. 60/104,842 filed Oct. 20, 1998 and Ser. No. 60/165,608 filed Nov. 15, 1999 and is a continuation-in-part of Ser. No. 09/275,319 filed Mar. 24, 1999, now U.S. Pat No. 6,378,527.

FIELD OF THE INVENTION

The herein disclosed invention finds applicability in the field of cell culture, as well as in the field of tissue substitutes for tissue replacement and for prosthesis.

BACKGROUND

Attempts at replacing or rebuilding diseased or damaged structures in the human body go back to 3000 B.C. It was not until the middle of the 1900's, however, that the use of synthetic materials for rebuilding body structures met with widespread and reproducible success. Advances in material science and biomaterials and science have afforded much of the success. The need for new and better implants exists in every field of medicine in which disease or trauma can be treated surgically.

As technology advances continue to improve the state of the art, the standards for successful implants continue to improve including strength, biocompatibility and elasticity. The new research being conducted today on growth factors and controlled drug release tell of the day when implant material will be expected to promote healing, dissipate disease and stimulate tissue regeneration.

The inventors have continued to make improvements to more efficiently produce good quality cells and of sufficient quantity which are able to be transplanted effectively.

Beta-1 Integrin Immunolocalization on Human Chondrocytes Attached to Collagen Microcarriers Introduction: Interactions between the extracellular and the intracellular environment are known to be mediated by transmembrane glycoprotein receptors called integrins. Consisting of alpha and beta chains, integrins are non-covalently bonded protein complexes. These proteins are present in a whole array of cells, including human chondrocytes. Integrins are known to mediate cell attachment and are also involved in cell signaling pathways (Boudreau[1]). It has been documented that cartilage homeostasis and metabolism is highly influenced by the interaction between the chondrocytes and the extracellular matrix. The role of integrins as mediators of this interaction on chondrocytes has recently been reported (Lapadula[2]). It has also been documented that the expression of integrin chains may be inversely correlated to the degree of damage in pathological conditions such as osteoarthritis (Lapadula[2]).

It has been previously reported that human articular chondrocytes propagated in microcarrier spinner culture produce the extracellular matrix components collagen type II and proteoglycans more actively than cells in monolayer culture (Frondoza[3]). The mechanism by which the microcarrier spinner culture promotes the chondrocytic phenotype is not clear. The present study tests the hypothesis that maintenance of chondrocytic phenotype in microcarrier spinner culture may involve integrin β1. The inventors have immunolocalized integrin β-1 while the cells are still attached to the collagen beads. The main goal was to visualize the expression of integrin β-1 on chondrocytes without disrupting the cell-material interaction.

Methods: Cartilage was obtained from two different tissue sites: (a) knee cartilage from osteoarthritic patients at the time of total knee replacement, (b) nasal cartilage from patients during nasal septum reconstruction. Chondrocytes isolated by collagenase digestion were directly seeded at $4\times10^3$ cells/cm$^2$ onto collagen microcarriers (Cellagen™ 100–400 $\mu$m derived from bovine corium, ICN, Cleveland, Ohio) previously described (Frondoza[3]). Microcarrier spinner cultures were incubated at 37° C., 5% $CO_2$ for fourteen days. Chondrocytes were sedimented in conical tubes and then aliquoted onto microscope slides. Viability of chondrocytes was determined using trypan blue vital dye. Chondrocytes were transferred to microscope slides, fixed with 2% paraformaldehyde, and air-dried. Chondrocytes on microcarriers were then immunostained using immunoperoxidase with monospecific antibodies for β1 (Chemicon International, Inc.), collagen types I and II (Fisher Scientific, Pittsburgh, Pa.); and keratan sulfate (ICN Biomedicals, Inc., Aurora, Ohio).

Total RNA was isolated by the TRIzol Reagent method (Life Technologies, Rockville, Md.). A total cDNA library was synthesized using the Advantage RT-PCR Kit (Clontech Laboratories, Palo Alto, Calif.) with the Oligo $(dT_{18})$ primer. The resulting reverse transcriptase product was expanded using the SuperTaq Plus (Ambion, Austin, Tex.) PCR Kit and specific primers for collagen type II, type I, aggrecan and the housekeeping genes GADPH and ribosomal RNA S14 subunit. The PCR products were analyzed by agarose gel electrophoresis.

Results: Cells attached to the surface of microcarriers remained viable after two weeks in culture. Chondrocytes isolated from knee or nasal cartilage displayed similar growth patterns and immunostaining characteristics. Microcarriers are seen covered by cells with their surrounding dense extracellular matrix. Many microcarriers exhibited halo-like outgrowths of cells with their matrix-like material. Cells on microcarriers stained more intensely for integrin β, collagen type II, and keratan sulfate. Microcarriers were seen forming clusters of up to 8 beads. There was insignificant staining for collagen type I, and also when the primary antibodies were omitted. Expression of β1 integrin, collagens type I and II and proteoglycans was verified with the RT-PCR semi-quantitative analysis.

The inventors have found that β1 integrin is strongly co-expressed with collagen type II and proteoglycans by chondrocytes on microcarrier spinner culture. Cell inside-out and outside in signaling, as well as regulation of extracellular matrix metabolism, have been documented to be integrin-mediated (Lapadula[2]). Microcarrier spinner culture, a biomechanically active environment, may promote and enhance integrin β1 expression on chondrocytes, as well as their participation in the maintenance of the original chondrocyte phenotype. The inventors intend to employ integrin expression as a measure of viability of chondroctyes.

Collagen Microcarriers Support the Phenotypic Expression of Chondrocytes from Human Knee, Nasal, and Ankle Cartilage Introduction: A novel approach to repair articular cartilage currently being investigated, is cell therapy. Cells are transplanted by themselves or transplanted in a delivery vehicle such as resorbable polymers. As an avascular and alymphatic tissue, articular cartilage does not adequately heal and the repair tissue is frequently fibrocartilage. The repair consists primarily of collagen type I, rather than collagen type II which is characteristic of hyaline articular cartilage. The proteoglycan content is altered from high (aggrecan) to low molecular weight. The inability of cartilage to heal is also attributed to the limited capacity of chondrocytes, the only cellular constituent of cartilage to proliferate and produce components of the surrounding extracellular matrix (Buckwater[4]). Alteration in the chemical composition of articular cartilage leads to physical changes that compromise the biomechanical function of the joint.

A major problem in the use of cell-based therapy is the limited number of cells capable of producing the appropriate extracellular matrix that constitute hyaline cartilage. The inventors have propagated chondrocytes from three distinct cartilaginous tissues: the knee, nose, and ankle. Propagation has taken place on collagen microcarriers using the suspension spinner culture technique. Collagen microcarrier spinner culture promotes the chondrocytic phenotype of cells retrieved from different cartilage sites. It is obvious that additional tissue sources of chondrocytic cells are desirable and provide additional donor pool of cells for articular cartilage repair. This is a major object of this invention.

Cartilage was obtained from three different tissue sites: (a) knee cartilage from 5 osteoarthritic patients at the time of total knee replacement, (b) ankle cartilage from 5 patients with vascular disease undergoing below the knee amputation, and (c) nasal cartilage from 5 patients during nasal septum reconstruction. Chondrocytes isolated by collagenase digestion were directly seeded at $4 \times 10^3$ cells/cm$^2$ onto Cellagen microcarriers (100–400 μm derived from bovine corium, ICN, Cleveland Ohio) or as monolayer culture as previously described. Monoalyer and microcarrier spinner cultures were incubated at 37° C., 5% $CO^2$ for fourteen days. Chondrocytes were harvested and cell samples enumerated in trypan blue vital dye or were cytocentrifuged onto microscope slides using Cytospin II (Shandon Lipsha). The cytospun cells were immunostained using monospecific affinity purified antibodies to collagen types I and II (Fisher Scientific, Pittsburgh, Pa.); and for proteoglycans using monospecific antibodies to: keratan (ICN Biomedicals, Inc., Aurora, Ohio), chondroitin-4, chrondotin-6 sulphate and unsulphated chondroitin. The rest of the cells were frozen for subsequent RNA isolation.

Total RNA was isolated by the TRIzol Reagent method (Life Technologies, Rockville, Md.). A total cDNA library was synthesized using the Advantage RT-PCR Kit (Clontech Laboratories, Palo Alto, Calif.) with the Olgio (dT$_{18}$) primer. The resulting reverse transcriptase product was expanded using the SuperTaq Plus (Ambion, Austin, Tex.) PCR Kit and specific primers for collagen type II, type I, aggrecan and the housekeeping genes GAPDH and ribosomal RNA S14 subunit. The PCR products were analyzed by agarose gel electrophoresis.

Chondrocytes isolated from knee, nasal and ankle cartilage proliferated in matching monolayer and microcarrier spinner culture. Within two weeks, cell numbers increased up to 12 fold in monolayer culture while cells multiplied up to 17 fold in microcarrier spinner culture.

The inventors found that chondrocytes taken directly from knee, nasal or ankle cartilage expressed collagen type II and aggrecan but not collagen type I. Tests show representative RT-PCR profiles of mRNA expression, of matched monolayer and spinner cultures. Propagation of chondrocytes from three cartilage sites in suspension or spinner culture maintained the expression of collagen type II while decreasing the expression of collagen type I. In contrast, propagation of matching chondrocytes in monolayer culture increased the expression of collagen type I. There was no detectable change in aggrecan expression when chondrocytes were propagated either as monolayer or spinner culture. The intensity of immunostaining for collagen type I also increased in chondrocytes from all three cartilage sites propagated as monolayer cultures. The immunostaining pattern of collagen type II, and proteoglycans appeared the same under both culture conditions.

The present study confirms the advantage of propagating chondrocytes in collagen microcarrier spinner culture and that chondrocytes retrieved from cartilaginous sites of the nose, knee and ankle are able to multiply and maintain features of their original phenotype. This observation suggests the possibility that other cartilaginous tissue donor sites may provide functional chondrocytes. Availability of chondrocytes capable of producing extracellular matrix that resembles articular cartilage offers an alternative approach for cell-based repair of cartilage defects. Knee, nose and ankles are attractive sources of chondrocytes and will facilitate greatly in accomplishing the objectives of this invention.

De Novo Synthesis of $\beta_1$ Integrin Expression by Human Chondrocytes Propagated on a Flexible Silicone Membrane and Subjected to Cyclic Mechanical Strain Articular chondrocytes possess the ability to sense and respond to changes in their mechanical environment, although the cellular mechanisms by which this phenomenon occurs are not fully understood. One possible pathway involves the $\beta_1$ integrins, which have been shown to mediate binding of chondrocytes to a variety of matrix components [Salter[5]]. Few studies have examined the effect of mechanical stimulation on integrin expression by chondrocytes. Holmvall[6] analyzed $\beta_1$ integrin mRNA expression by chondrocytes and found no change or a decrease in response to applied cyclic strain. The purpose of the present study was to determine, using metabolic labeling and immunoprecipitation techniques, whether cyclic mechanical strain applied to human chondrocytes in an in vitro culture system could modulate de novo synthesis of $\beta_1$ integrins.

Methods: Non-fibrillated articular cartilage was obtained from the knees of two patients undergoing total knee arthroplasty. Chondrocytes were isolated by collagenase digestion, seeded onto type I collagen microcarriers in siliconized spinner flasks or into monolayer culture and incubated at 37° C., 5% $CO_2$ for 14 days. Previously (Frondoza[3]) showed that chondrocytes grown in a microcarrier spinner culture system proliferate and retain their chondrocytic phenotype. Chondrocytes were harvested from the microcarriers or monolayer cultures, plated onto type I collagen-coated flexible-bottom wells (Flexcell International), and allowed to adhere for 48 h. For the final 4 h, the cells were incubated in cys-free, met-free medium. 20 μCi/ml of [$^{35}$S]-labeled cysteine and methionine was then added to each well, and the wells were subjected to cyclic strain at 0.5 Hz, using a computer-controlled strain apparatus with a vacuum pressure of −20 kPa; replicate samples were maintained under static conditions. After mechanical stimulation, the cells were lysed using buffered 1% Triton X-100 and precleared with 15 μl protein G-agarose for 1 h. Following centrifugation, the supernatant from each sample was reacted with murine anti-$\beta_1$ monoclonal antibody and 15 μl protein G-agarose for 2 h. Each sample was then eluted from the agarose beads by boiling, separated by SDS-PAGE, and analyzed by autoradiography.

RNA was isolated from trypsinized cells and used to create a total cDNA library. Aliquots of the reverse transcriptase product were then expanded by PCR, using primers for the integrin sequence as well as the housekeeping gene S14 (to ensure loading of equal volumes). The PCR products were analyzed by agarose gel electrophoresis.

With cells grown in monolayer culture, autoradiography of the immunoprecipitation products revealed dark bands corresponding to $\beta_1$ integrin subunits and fainter bands corresponding to coprecipitated a subunits, as determined by comparison with $^{14}C$ molecular weight standards. Mechanical stimulation produced no significant change. In contrast, cells from spinner culture maintained under static conditions exhibited a faint $\beta_1$ band while mechanical flexing produced intense $\beta_1$ and $\alpha$ bands. In controls using goat anti-chicken IgG as an irrelevant antibody, no integrin bands were seen. In both monolayer and spinner culture cells, RT-PCR revealed no change in mRNA expression in response to mechanical strain.

This study demonstrates that de novo synthesis of $\beta_1$ integrins by cultured human chondrocytes can be increased by applied cyclic strain. This effect was more pronounced in cells grown in spinner culture, which under static conditions exhibit lower levels of $\beta_1$ integrin expression than cells from monolayer. No change in mRNA expression was seen, suggesting that this response is a post-translational event, consistent with previous findings [Holmvall[6]]. These observations suggest that $\beta_1$ integrins are involved in mediating the response of chondrocytes to changes in their mechanical environment. Cyclic strain during culture of chondroctyes will produce chondrocytes which are more effective for transplantation.

Differential Integrin Expression by Human Chondrocytes Propagated on a Flexible Silicone Membrane Introduction: The ability of chondrocytes to sense and respond to changes in their mechanical environment depends on interactions between the cells and the cartilage extracellular matrix. These interactions are mediated by the integrin family of cell surface proteins [Salter[5], Lapadula[2]]. The inventors we have shown that chondrocytes propagated on type I collagen microcarriers in a spinner suspension system proliferate and maintain their chondrocytic phenotype [Frondoza[3]]. The purpose of the present study was to characterize, using immunofluorescence techniques, integrin expression by chondrocytes grown in a spinner culture system or in monolayer culture and then propagated on flexible silicone membranes, both in the presence and absence of applied cyclic mechanical strain.

Methods: Non-fibrillated articular cartilage was obtained from the knees of patients undergoing total knee arthroplasty. Chondrocytes were isolated by collagenase digestion, seeded onto type I collagen microcarriers in siliconized spinner flasks or-into monolayer culture and incubated at 37° C., 5% $CO_2$ for 14 days. Cells were then harvested from the microcarriers or monolayer cultures and plated onto type I collagen-coated flexible-bottom wells (Flexcell International). After allowing the cells to adhere for 48 h, the wells were subjected to cyclic strain at 0.5 Hz, using a computer-controlled strain apparatus with a vacuum pressure of −20 kPa; replicate samples were maintained under static conditions. Cells were recovered from the wells by digestion with 0.25% trypsin and reacted with murine monoclonal antibody specific for human $\beta_1$, $\alpha_5$, or $\alpha_v$ integrin subunit followed by FITC-conjugated goat anti-mouse F(ab')$_2$ fragment. After fixation with 2% paraformaldehyde, $10^4$ consecutive cells from each sample were analyzed by flow cytometry, with the results expressed as a histogram with respect to fluorescence intensity. Mean fluorescence of each sample was estimated by the position (channel number) of the peak of the unimodal histogram. In addition, cells stained for $\beta_1$ were analyzed by laser-scanning confocal microscopy.

Results as shown in FIG. 1: For two cases with matched monolayer and spinner cultures, $\beta_1$ integrin expression by chondrocytes propagated in monolayer was 1.8–5.5 times higher than that of cells from spinner culture, as determined by comparison of the flow cytometry histograms. In one case, sufficient cells were available for analysis of $\alpha_5$ and $\alpha_v$ expression, which were 10% and 37% higher, respectively, in cells from monolayer as compared to spinner culture. Mechanical flexing had a variable effect on $\beta_1$ integrin expression by chondrocytes in monolayer, with a 17% decrease in fluorescence in one case and a 15% increase in the other case (FIG. 1), as compared with static controls. In contrast, mechanical flexing of chondrocytes from spinner culture resulted in a consistent 21–50% increase in $\beta_1$ expression (FIG. 1). With the a subunits, mechanical flexing of cells from spinner culture resulted in 5% and 36% increases, respectively, in $\alpha_5$ and $\alpha_v$ expression, while monolayer cells underwent decreases of 13% and 5%. Confocal microscopy revealed diffuse membrane staining for $\beta_1$ subunit, with more intense staining seen in cells from monolayer culture. Mechanical stimulation resulted in a greater increase in staining, however, in cells from spinner culture.

This study demonstrates that $\alpha_1$, $\alpha_5$, and $\alpha_v$ integrin expression by human chondrocytes in vitro can be modulated by culture conditions. Specifically, chondrocytes grown in monolayer, which gradually assume a more fibroblastic phenotype, express higher levels of integrins on their surface than chondrocytes propagated in microcarrier spinner culture, with the most pronounced effect seen with the $\beta_1$ subunit. However, cells from spinner culture (which maintain a chondrocytic phenotype) exhibit a relatively greater increase in integrin expression in response to applied cyclic strain, while cells grown in monolayer had a variable response. These results suggest that integrins are involved in mediating the response of chondrocytes to changes in their mechanical environment. Spinner culture along with cyclic strain are visualized as being able to produce better quality chondrocytes.

CHONDROCYTE SEEDED CHITOSAN SCAFFOLDS

Chondrocytes, the cellular constituent of cartilage, have a limited capacity to proliferate but are metabolically active. Following trauma or disease, damaged cartilage oftentimes does not heal. An approach for solving this problem is to repair cartilage defects by transplantation of tissue-engineered biomaterials that can substitute for damaged cartilage. This material can be seeded with chondrocytic cells capable of producing cartilaginous tissue. The tissue engineered product thus consists of cells delivered in a scaffold. Several types of scaffolds are being investigated for cell seeding including collagenous materials and resorbable polymers. However, each of these has limitations, thus there is still the need to identify an appropriate material.

The natural polymer chitosan is a potential candidate as a biocompatible chondrocyte scaffold. Chitosan is the product of the partial deacetylation of the natural polysaccharide chitin, which is found in the exoskeletons of insects and marine invertebrates. Chitosan has been suggested to possess biological and material properties suitable for clinical applications. It is reported to be non-toxic and bioresorbable when used in human and animal models. Previous work in this laboratory has demonstrated that cells cultured on chitosan-coated surfaces remain viable and maintain a morphology similar to that displayed by osteoblasts and chondrocytes in vivo (Lahiji[8]). Based on these observations, we hypothesize that chitosan can serve as a supporting scaffold for the growth of chondrocytic cells. The purpose of this study was to identify a chitosan formulation that promotes the growth and extracellular matrix production of chondrocytes.

Materials and Methods: Seven different formulations of chitosan were evaluated. Preparation "A" consisted of 3% (w/v) chitosan in 1M HAC neutralized with sodium bicarbonate and then immersed in a methanol solution. Preparation "B" was produced by sandwiching a chitosan solution [2% (w/v) in 49% (v/v) water and methanol solution] between two layers of solid sodium bicarbonate. Preparation "C" was prepared by the phase inversion method in which 3% chitosan in 1M HAC was immersed in an excess of methanol for 5 days. Preparation "D" was prepared by mixing a 3% chitosan solution with an excess of sodium bicarbonate to form a paste. The bicarbonate was removed and the material was placed into a 1M NaOH solution, then washed in deionized water. Preparations "E"–"G" were frozen as 1.00% ("E"), 1.25% ("F"), and 1.5% ("G") chitosan solutions. The solutions were subsequently placed in 1M NaOH, and then washed in phosphate buffer to obtain a physiological pH. The gels were refrozen for lyophilization. In all cases except for preparation "B", chitosan was dissolved in 1M acetic acid.

Chondrocytes were isolated from: (a) articular cartilage retrieved from osteoarthritic patients undergoing total knee replacement; and (b) nasal cartilage from patients undergoing nasal septum reconstruction. Chondrocytes isolated by collagenase digestion were propagated by seeding $4 \times 10^3$ cells/cm$^2$ onto Cellagen microcarrier (100–400m derived from bovine corium, ICM, Cleveland Ohio). Spinner cultures were incubated at 37° C., 5% $CO_2$ until ready for use. Chitosan sponges were cut into 0.5 cm$^3$ cubes and then seeded with $1 \times 10^6$ cells in 40 $\mu$l of media. They were analyzed at various time points after seeding. Replicate sponges were paraffin embedded for H-E and toluidine blue staining. Another set of sponges was OCT embedded for frozen sections. Collagen and proteoglycans were visualized by using monospecific antibodies against collagen types I, II and keratan sulfate. To analyze proteoglycans, the seeded sponges were pulsed for 60 hours with 50 $\mu$Ci/mL $^{35}SO_4$. The proteoglycans were extracted from both the spent media and the sponges using 4M guanidinium HCl for 24 hours at 4° C. The extracts were dialysed against $ddH_2O$ to remove unincorporated label. The Dc protein assay from BioRad was used to assess protein concentration in the cell associated fractions (CAF). The protein concentration in CAF was used to normalize the total CPM in each fraction.

Results: Of the seven chitosan formulation tested, preparations "E" (1%) and "F" (1.25%) best facilitated cellular permeation and attachment. However, "E" was friable and fell apart with handling. Preparations "F" was firmer and could be manipulated with ease. Chondrocytes from knee or nasal cartilage infiltrated the "F" sponge readily. The seeded chondrocytes proliferated in the chitosan sponges. Chondrocytes exhibited spherical morphology surrounded by an amorphous extracellular matrix-like material. They displayed intense immunostaining for collagen type II and keratan sulfate. Immunostaining for collagen type I was insignificant. The specificity of the staining was verified by omitting the primary antibodies or by substituting irrelevant anti-human Ig antibody.

Figure 2:
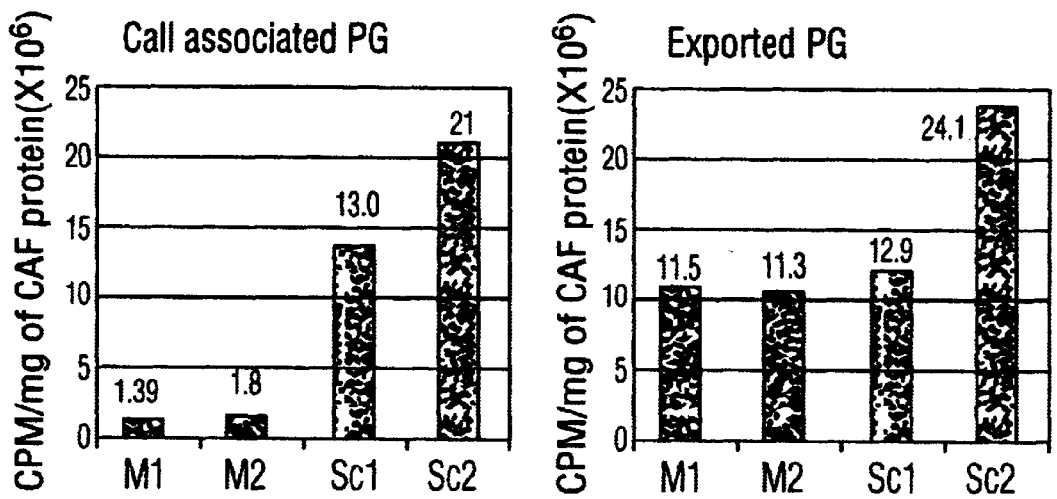

Analysis of $^{35}SO_4$ incorporation showed that chondrocytes-seeded in replicate chitosan "F" scaffolds (Sc1 and Sc2) synthesized proteoglycans more actively than matching chondrocytes propagated in monolayer ($M_1$, $M_2$) culture (FIG. 2). Newly synthesized proteoglycans were detectable in the cell associated fractions and were also exported to the medium.

Human chondrocytes propagated in microcarrier spinner culture and then seeded into chitosan scaffolds multiplied and continued synthesis of collagen II and proteoglycans. That chondrocytes continue to produce the extracellular matrix-like material similar to hyaline cartilage indicates that the chitosan "F" sponge formulation is an attractive candidate for preparation of cell-material construct. Availability of a biocompatible tissue engineered construct would be useful for repairing cartilage defects.

Arabinogalactan-Chitosan Polymers as Chondrocyte Scaffolds for Repair of Cartilage Defects Recent development in tissue engineering has focused on the potential use of cell-seeded scaffolds for the repair of articular cartilage. Articular cartilage is unique in that it has limited capacity to heal and attempts to repair results in formation of fibrocartilage. The repair tissue has altered biochemical and physical properties, which compromises the mechanical function of the joint. An approach for solving this problem is to repair cartilage defects by transplantation of tissue-engineered biomaterials that can substitute for damaged cartilage.

Arabinogalactan-chitosan polymers and particularly dialdehyde arabinogalactan (DAAG) are an attractive candidate to serve as biocompatible chondrocyte scaffolds. Dialdehyde arabinogalactans (DAAG) are highly branched natural polysaccharide whereas chitosan is the product of the partial deacetylation of chitin, which is found in the exoskeletons of insects and marine invertebrates. Both dialdehyde arabinogalactans (DAAG) and chitosan have been suggested to possess biological and material properties suitable for clinical applications (Falk[7], Lahiji[8]). They are non-toxic and bioresorbable when used in human and animal models. Previous work in this laboratory has demonstrated that cells cultured on chitosan-coated surfaces remain viable and maintain morphology similar to that displayed by osteoblasts and chondrocytes in vivo (Frondoza[3]). Based on these observations, the inventors hypothesize that DAAG-chitosan polymeric construct could serve as supporting scaffold for the growth of chondrocytic cells. The purpose of this study was to determine whether DAAG-chitosan polymers constructs could support the growth and extracellular matrix production of human articular chondrocytes.

Materials and Methods:

Dialdehyde arabinogalactans (DAAG) were mixed with 2% v/v chitosan in acetic acid at 5%, 10%, 20% or 40%. The mixtures were stirred at 37° C. for 3 to 5 days and the physiological pH was adjusted with NaOH. Another set of the same preparations was reduced using sodium borohydride. The final mixtures were then washed and lyophilized.

Specific examples of preparing dialdehyde arabinogalactan (DAAG) conjugated with Chitosan were as follows:

1. A solution of chitosan was prepared by dissolving chitosan in 2% v/v acetic acid. After the chitosan was fully dissolved, 10% w/w DAAG was added to the chitosan solution. The reaction was shaken at 37° C. for 5 days, and the pH was gradually raised to 5 with NaOH solution. The gel resulting from this reaction was lyophilized, washed with water and lyophilized again.

2. A solution of chitosan was preparing by dissolving chitosan in 2% v/v acetic acid. After the chitosan was fully dissolved, 10% w/w DAAG was added to the chitosan solution. The reaction was shaken at 37° C. for 5 days, and the pH was gradually raised to 5 with NaOH solution. Reduction was performed by adding sodium borohydride to the formed gel. The reaction was shaken overnight and the gel lyophilized, washed with water and lyophilized again.

3. A solution of chitosan was prepared by dissolving chitosan in 2% v/v acetic acid. After the chitosan was fully dissolved, 5% w/w DAAG was added to the chitosan solution. The reaction was shaken at 37° C. for 5 days, and the pH was gradually raised to 5 with NaOH solution. The gel resulting from this reaction was lyophilized, washed with water and lyophilized again.

4. A solution of Chitosan was prepared by dissolving chitosan in 2% v/v acetic acid. After the chitosan was fully dissolved, 5% w/w DAAG was added to the chitosan solution. The reaction was shaken at 37° C. for 5 days, and the pH was gradually raised to 5 with NaOH solution. Reduction was performed by adding sodium borohydride to the formed gel. The reaction was shaken overnight and the gel was lyophilized, washed with water and lyophilized again.

5. A solution of chitosan was prepared by dissolving chitosan in 2% v/v! acetic acid. After the chitosan was fully dissolved, 20% w/w DAAG was added to the chitosan solution. The reaction was shaken at 37° C. for 5 days, and the pH was gradually raised to 5 with NaOH solution, then the gel was lyophilized, washed with water and lyophilized again.

6. A solution of chitosan was prepared by dissolving chitosan in 2% v/v acetic acid. After the chitosan was fully dissolved, 20% w/w DAAG was added to the chitosan solution. The reaction was shaken at 37° C. for 5 days, and the pH was gradually raised to 5 with NaOH solution. Reduction was performed by adding sodium borohydride to the formed gel. The reaction was shaken overnight and the gel was lyophilized, washed with water and lyophilized again.

Chondrocytes were isolated from articular cartilage retrieved from osteoarthritic patients undergoing total knee replacement. Chondrocytes isolated by collagenase digestion were propagated by seeding $4 \times 10^3$ cells/cm$^2$ onto Cellagen microcarrier (100–400m derived from bovine corium, ICM, Cleveland Ohio). Spinner cultures were incubated at 37° C., 5% $CO_2$ until ready for use (2). DAAG-chitosan sponges were cut into 0.5 cm$^3$ cubes and then seeded with $1 \times 10^6$ cells in 40 µl of media. They were analyzed at various time points after seeding. Replicate sponges were paraffin embedded for H-E and toluidine blue staining. Another set of sponges was OCT embedded for frozen sections. Collagen and proteoglycans were visualized by using monospecific antibodies against collagen types I, II and keratan sulfate. To analyze proteoglycans, the seeded sponges were pulsed for 60 hours with 50 µCi/ml $^{35}SO_4$. The proteoglycans were extracted from both the spent media and the sponges using 4M guanidinium HCl for 24 hours at 4° C. and radiolabel incorporation was determined by liquid scintillation counting. Aliquots were electrophoresed on 0.6% agarose-1.2% polyacrylamide gels and then autoradiographed. The Dc protein assay from BioRad was used to assess protein concentration in the cell-associated fractions (CAF). The protein concentration in CAF was used to normalize the total CPM in each fraction.

Figure 3:
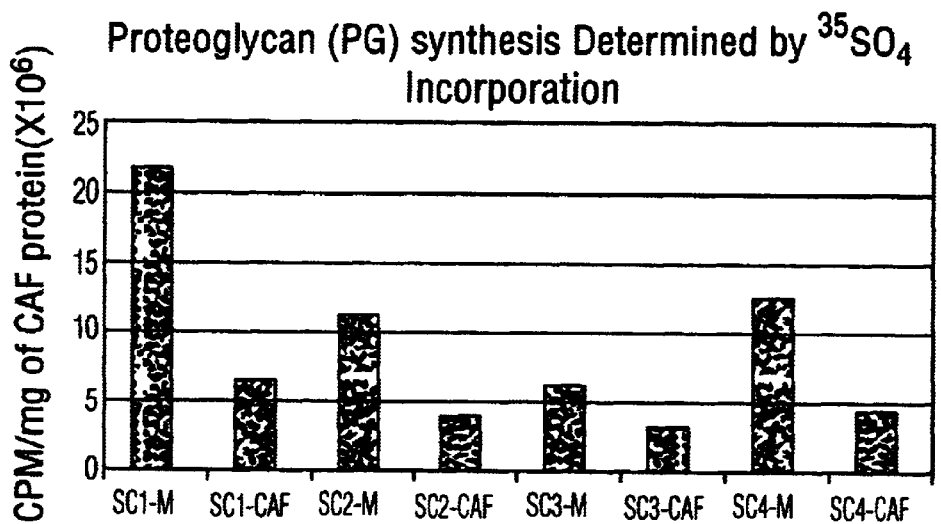

Results: All DAAG-chitosan formulations adjusted to physiological pH and retained their firm 3-dimensional structure to over two weeks in culture. They facilitated cellular permeation and attachment. There was no detectable toxic effect on any of cell-seeded constructs. The seeded chondrocytes proliferated in the DAAG-chitosan scaffolds indicated by the presence of cell clusters after two-weeks of culture. Chondrocytes exhibited spherical morphology surrounded by an amorphous extracellular matrix-like material. They displayed intense immunostaining for collagen type II and keratan sulfate. Immunostaining for collagen type I was insignificant. The specificity of the staining was verified by omitting the primary antibodies or by substituting irrelevant anti-human Ig antibody. Active de novo proteoglycan synthesis was verified by $^{35}SO_4$ incorporation in DAAG-chitosan scaffolds (SC1=5% DAAG; SC2=20% DAAG; SC3=20% DAAG-reduced; SC4=40% DAAG) shown in FIG. 3. Newly synthesized proteoglycans were detectable in the cell-associated fractions and were exported to the medium. These newly synthesized proteoglycans had high molecular weights similar to aggrecan, which is an identifying marker for hyaline cartilage (lanes 2–5, FIG. 3 bottom panel). Chondrocytes propagated in microcarriers produced proteoglycans of similar sizes.

The inventors have discovered that DAAG-chitosan polymers can successfully support the proliferation and matrix production of human articular chondrocytes. These cells multiply and synthesize collagen II as well as proteoglycans. That chondrocytes continue to produce the extracellular matrix-like material similar to hyaline cartilage indicates that the DAAG-chitosan polymers are an attractive candidate for preparation of cell-material construct. Availability of a biocompatible tissue engineered construct would be useful for cartilage repair.

Tissue Engineered Body Part Replacement

The invention also relates to a method of stimulating the proliferation and appropriate cell maturation of a variety of different cells and tissues in three-dimensional cultures in vitro using special cell culture techniques. In accordance with the invention, stromal cells, including, but not limited to, chondrocytes, chondrocyte-progenitors, fibroblasts, fibroblast-like cells, umbilical cord cells or bone marrow cells from umbilical cord blood and stem cells are obtained and inoculated and grown on a three-dimensional framework. Stromal cells may also include other cells found in loose connective tissue such as endothelial cells, macrophages/manocytes, adipocytes, pericytes, reticular cells found in bone marrow stroma, etc.

The invention also relates to the growth and preparation of cartilage in vitro which can be used for a variety of purposes in vivo. In accordance with the invention, stromal cells which elaborate cartilage-specific macromolecules and extracellular atrix proteins, can be inoculated and grown on three dimensional frameworks or biodegradable scaffolds. The stromal cells, which are inoculated onto the scaffold, may include chondrocytes, chondrocyte-progenitors, fibroblasts, fibroblast-like cells and/or cells capable of producing collagen type II and other collagen types, and proteoglycans which are typically produced in cartilaginous tissues.

The cells are to be grown on the scaffold in a sterile environment. The use of pressure is foreseen as being beneficial for cell growth on the scaffold. Spin-culture or rotation is seen as enhancing cell growth and harvesting. Low oxygen concentration or alternating high and low oxygen culture is seen as being efficacious.

In accordance with the invention, stromal cells are inoculated onto a three-dimensional framework network or scaffold, and grown in culture to form a living cartilaginous material. The stromal cells may comprise chondrocytes, chondrocyte-progenitors, fibroblasts or fibroblast-like cells with or without additional cells and/or elements described more fully herein. The chondrocytes, fibroblast-like cells and other cells and/or elements that comprise the stroma may be fetal or adult in origin, and may be derived from convenient sources such as cartilage, skin, etc. Umbilical cord and placenta tissue or umbilical cord blood may serve as an advantageous source of fetal-type stromal cells, e.g., chondrocyte-progenitors and/or fibroblast-like cells for use in the three-dimensional system of the invention. Examples of cells useful for practicing this invention are pluripotential cells, mesenchymal cells, stem cells and other types of progenitor cells.

Isolation of Bone Marrow Cells and Purification of Mesenchymal Stem Cells

Bone marrow aspirates will be obtained aseptically during primary joint replacement from osteoarthritic patients, or from normal donors. Cells will be collected into heparinized syringes to a final concentration of 1000 $\mu$/mL of aspirate. The cell in suspension will be layered onto 10 mL of Ficoll-Pogue gradient in a conical 50 mL sterile disposable tube. The gradient will be centrifuged at 200 g at 4° C. for ten minutes. Cells at the interface will be collected and then washed with Hank's™ balanced salt solution. The washed cells containing the mesenchymal stem cells will then be resuspended in HY media (Frondoza, Cancer Research 1988). An aliquot of cells will be diluted with Trypin blue dye and enumerated to determine viability and cell number. The cell number will be adjusted and then plated at a cell density of ~$1 \times 10^7$/mL/flask. Media will be replaced twice a week until the culture becomes confluent at ~2 weeks. After reaching confluence, the supernatant fluid containing non-adherent cells and cellular debris will be discarded. The adherent cells will be harvested using 0.05% trypsin, 0.53 m MEDIA for five minutes. The retrieved cells will be washed in Hank's™ balanced salt solution for subsequent chondrogenic culture.

Propagation of Mesenchymal Stem Cells (MSC) on Microcarriers

This technique has been previously described in detail for the propagation of human articular chondrocytes; the procedure used to culture human chondrogenic mesenchymal stem cells is essentially the same (Frondoza, et al, 1996). Briefly, cells will be converted to chondrocytes first as monolayer culture in enriched Dulbecco minimal essential medium, supplemented with chondrogenic factors such as TGF-$\beta$ and containing 20% fetal calf serum, and propagated until confluence, as described above. The cells will be harvested by trypsinization, counted, and assayed for viability. Cells will be subsequently seeded onto collagen microcarrier beads (Cellagen™ 100–400 $\mu$m derived form bovine corium, ICN, Cleveland, Ohio) at a density of $4 \times 10^3$ chondrocytes/cm$^2$ in a siliconized spinner flask. During the first four hours, the mixture will be intermittently stirred for two minutes every 30 minutes at 25–30 rpm. The cell-microcarrier suspension will be subsequently stirred at 45 rpm for another four hours. The speed will be gradually increased to 60 rpm and then maintained at 60 rpm for the duration of the culture. The final volume of the suspension culture will be 30 mL per $1 \times 10^6$ cells. To replenish the spinner cultures, the microcarriers will be sedimented for five minutes and approximately 50% of the spent medium will be replaced every three days. Spinner cultures will be incubated at 37° C., 5% $CO_2$. The most optimal condition to promote chondrogenesis will be determined by addition of growth factor TGF-$\beta$3, with or without 20% fetal calf serum. Alternatively, MSC will be expanded in monolayer culture harvested by trysinization and subsequently seeded out collagen microcarrier beads and then cultured in chondrogenic melia to convert the cells to chondrocytes.

In practicing this invention, the preferred scaffold will be fashioned from chitosan, dialdehydearabinogalactan or a mixture of chitosan and dialdehydearabinogalactan.

The invention involved methods, compositions of matter and articles for transplantation comprising culturing stem cells and inoculating the resulting cell on the scaffold of this invention.

In view of the above disclosure, the herein disclosed invention envisions tissue-engineered replacement body parts for a patient, wherein cells from a body part have been grown, at least initially in the laboratory. The cells are to be cells of a sample obtained from tissue of the patient, and wherein the said cells of the body part have been grown in an environment of rotation and low oxygen concentration in the laboratory. The tissue-engineered replacement body part will further include a biodegradable scaffolding for preparing the body part. In addition, the tissue-engineered replacement body part wherein a sample tissue to obtain the cells is to be taken from the patient's nasal area or the nasal septum.

The inventive concept disclosed involves a tissue-engineered replacement body part for patient, wherein the cells to prepare the body part have been grown at least initially in the laboratory from a sample tissue obtained from the patient's nasal area or the nasal septum. The body part replacement can be for cartilage. The replacement cartilage will include a biodegradable polymer scaffolding for preparing the replacement cartilage. The tissue-engineered replacement body part will be derived from cells for producing the body part which cells have been grown in a rotational environment in the laboratory. As a further improvement, the tissue-engineered replacement body part will be obtained from cells of the body part which cells have been grown in an environment of reduced oxygen.

The herein disclosed invention encompasses a method of replacing a tissue or body part or filling a void in the head or neck by surgery, comprising the steps of obtaining a non-diseased cell sample from the respective patient's head and neck area, rapidly growing additional cells in a bioreactor and within a predetermined mold which is the mirror image of the patient's tissue, body part or void, such that a molded tissue or body part is produced, and surgically implanting the molded tissue or body part as a replacement in the patient's head and neck area, such that the molded tissue or body part regenerates therein and fuses with the adjacent tissues in the head and neck area of the respective patient. The cells can be obtained from the respective patient's nasal area, and can be chondrocytes. Further, the method includes a scaffold made from a biodegradable polymer for supporting the molded tissue or body part.

References:

1. Boudreau N., Jones P. L. Biochem 339:481–488, 1999.
2. Lapadula G., Iannone F., Zuccaro C., Grattagliano V., Covelli M., Patella V., Lo Bianco G., and Pipitone V. Clin and Exp Rheumatol 15:247–254, 1997.
3. Frondoza C., Sohrabi A., Hungerford D. Biomaterials 17:879–888, 1996.
4. Buckwalter et al. J Orthop. Res. 12:144–148, 1994.
5. Salter D M, Hughes D E, Simpson R, Gardner D L, *Br J Rheumatol* 31:231–234, 1992.
6. Holmvall K, et al, *Exp Cell Res* 221:496–503, 1995.
7. R. Falk, A. J. Domb, I. Polaceck. Antimicrob Agents Chemother 1975, 1999.
8. A. Lahiji et al. Trans. Of the Soc. For Biomat, 22:206, 1999.

What is claimed is:

1. The method of replacing a body part or filling a void in head and neck surgery, comprising the steps of obtaining a non-diseased, cell sample from a patient's head and neck area, rapidly growing such cells in a bioreactor and within a mold in which a replica of the patient's body part or void is produced, and surgically implanting the molded body part or void as a replacement in the patient's head and neck area, such that the molded body part or void replaces the missing body part or void and regenerates therein and fuses with the adjacent tissues in the head and neck area of the respective patient.

2. The method of claim 1, wherein the cell sample is obtained from the respective patient's nasal septum.

3. The method of claim 2 wherein the cells obtained are chondrocytes.

4. The method of claim 1 further including a scaffold made from a bio-degradable polymer for supporting the molded tissue or body part.

* * * * *